United States Patent [19]

Haseltine et al.

[11] Patent Number: 5,321,124
[45] Date of Patent: Jun. 14, 1994

[54] ART (REV) PROTEIN OF HUMAN T-CELL LEUKEMIA VIRUS

[75] Inventors: William A. Haseltine, Cambridge; Craig A. Rosen, Brookline; Joseph G. Sodroski, Cambridge; Wei C. Goh, Somerville, all of Mass.

[73] Assignee: Dana Farber Cancer Institute, Boston, Mass.

[21] Appl. No.: 995,948

[22] Filed: Dec. 18, 1992

Related U.S. Application Data

[60] Continuation of Ser. No. 538,189, Jun. 14, 1990, abandoned, which is a division of Ser. No. 865,151, May 20, 1986, Pat. No. 4,935,372.

[51] Int. Cl.$^5$ ............................................. C07K 13/00
[52] U.S. Cl. .................... 530/350; 530/395; 930/221; 930/220; 435/5; 435/235.1; 424/89
[58] Field of Search ............ 530/350, 403, 413, 826; 536/23, 72; 435/235.1, 236; 930/221; 424/89; 935/11

[56] References Cited

U.S. PATENT DOCUMENTS 4,289,690 9/1981 Pestka et al. .................... 530/351

OTHER PUBLICATIONS

Haseltine et al. 1988 Sci. Am. 259, 52–62 (Oct. issue).
Gallo et al. 1988 Nature, 333, 504.
Arya, et al., 1985, Science 229, p. 71.
Ratner et al. 1985, Nature 313,277–284.
Fisher et al. 1985, Nature 316,262–265.
Schlesinger et al. (eds.) 1982 In: *Heat Shock From Bacteria to Man.* Cold Spring Harbor Laboratory, Cold Spring Harbor, N.Y., pp. 387–394 and 405–411.
Robey et al. 1985, Science 228, 593–595.
Arya et al. 1985 Science 229, 69–73.
F. Barre-Sinoussi et al., Science 200:868 (1983).
R. C. Gallo et al., Science 224:500 (1984).
J. Schupbach et al., Science 224, 503 (1984).
M. G. Sarngadharan et al., Science 224, 506 (1984).
J. A. Levy et al., Science 225:840 (1984).
D. Klatzmann et al., Nature (London) 312:767 (1984).
M. Seligman et al., N.E. Jour. Med. 311:1286 (1984).
M. Popovic et al., Science 224:497 (1984).
Wain-Hobson, S. et al., Cell 40:9–19 (1985).
Sanchez-Pescudor, R. et al., Science 227:484–451 (1985).
Muesing, M. A. et al., Nature 313:450–458 (1985).
Veronese, F. et al., Science 229:1402–1405 (1985).
Kitchen, L. et al., Nature 312:367–370 (1984).
Schupbach, J. et al., Science 228:503–505 (1984).
Allan, J. S. et al., Science 228:1091–1093 (1985).

(List continued on next page.)

*Primary Examiner*—Christopher S. F. Low
*Attorney, Agent, or Firm*—David G. Conlin; Ronald I. Eisenstein

[57] ABSTRACT

A gene and gene product that regulates the expression of the capsidal envelope genes of HTLV-III/LAV and that can be used to regulate the expression of heterologous (non-viral) genes as well is disclosed. This art gene consists of two exons and can be used in creating nucleotide segments, vectors and cell lines. A new method for screening for compounds that inhibit the replication of HTLV-III is also described and comprises:

(1) transfecting a T-cell line with the HTLV-III art and env genes;
(2) thereafter, adding a preselected compound to the transformed cell line in increasing concentrations; and
(3) determining whether the compound effects the art function without being toxic to the cell.

An additional parameter to use in diagnosis of AIDS disease is also described. The use of the art gene and gene product in AIDS therapy is also disclosed.

4 Claims, 11 Drawing Sheets

OTHER PUBLICATIONS

Sodoroski, J. et al., Science 229:74–77 (1985).
Sodoroski, J. et al., Science 231:1549–1553 (1986).
Lee, T. H. et al., Science 23:1546–1549 (1986).
Allan, J. S. et al., Science 230:810–812 (1985).
Rosen, C. A. et al., Cell 41:813–823 (1985).
Dayton, A., et al., Cell 44:941–947 (1986).
Zagury, et al., Science 231:850–853 (1986).
Seligman, M. et al., N. Eng. Jour. Med. 311:1286–1292 (1984).
Sodroski, J. et al., Science 227:171–173 (1985).
M. Gottlieb, et al., N. Eng. Jour. Med. 305:1425 (1981).
H. Masur et al., 1981 N. Eng. J. Med. 305, 1431.
F. Siegal et al., 1981, N. Eng. J. Med. 305, 1439.
H. Lane, et al., 1983, N. Eng. J. Med. 309, 453.
J. Ziegler, et al., 1984 N. Eng. J. Med. 311, 565.
G. Shaw et al., Science 227:177 (1985).
D. Klatzmann et al., Science 225:54 (1984).
Rosen, C. A., et al., Nature 319:555–559 (1986).
Sodroski, J. et al., Nature 321:412–417 (1986).
Goh, W. C. et al., Journal of Virology, 61:2, 633–637 (Feb. 1987).
Knight, D. M., et al., Science 236:837–840 (May 1987).
Peterlin, B. M. et al., Biotechnology 6:7, 794–799 (Jul. 1988).

Coding Exon I

```
                                                                                        SD
5538  TAGGCATCTCCTATGGCAGGAAGAAGCGGAGAACAGGACGAAGACCTCCTCAAGGCAGTCAGACTCATCAAGTTTCTATCAAAGCAGTAAGTAG  5633
             M  A  G  R  S  G  D  S  D  E  D  L  L  K  A  V  R  L  I  K  F  L  Y  Q  S  S  K  *
```

Coding Exon II

```
              SA
7925  TAGGCAGGATATATTCACCATTATCGTTTCAGACCCACCTCCCAATCCCGAGGGGACCCGACAGGCCCGAAGGAATAGAAGAAGGTGAGAGAG  8020
      *  A  G  I  F  T  I  I  T  V  S  D  P  P  P  N  P  E  G  T  R  Q  A  R  R  N  R  R  R  W  R  E

BamHI
8021  AGACAGAGACACAGATCCATTCGATTAGTGAACGGATCCTTAGCACTTATCTGGGACACTATCTGCCGAGGCTGTGCCTCTTCAGTTACCACCCGCTTGAC  8116
      R  Q  R  Q  I  H  S  I  S  E  R  I  L  S  T  Y  L  G  R  S  A  E  P  V  P  L  Q  L  P  P  L  E

8117  AGACTTACTCTTGATTGTAACGAGGATTGTGAACTTCTGGGACGCAGGGGGTGGGAAGCCCTCAAATATTGGTGGAATCTCCTACAGTATTGGAG  8212
      R  L  T  L  D  C  N  E  D  C  G  T  S  G  T  Q  G  V  G  S  P  Q  I  L  V  E  S  P  T  V  L  E

8213  TCAGGAGCTAAAGAATAG  8230
      S  G  A  K  E  *
```

FIG. 1B

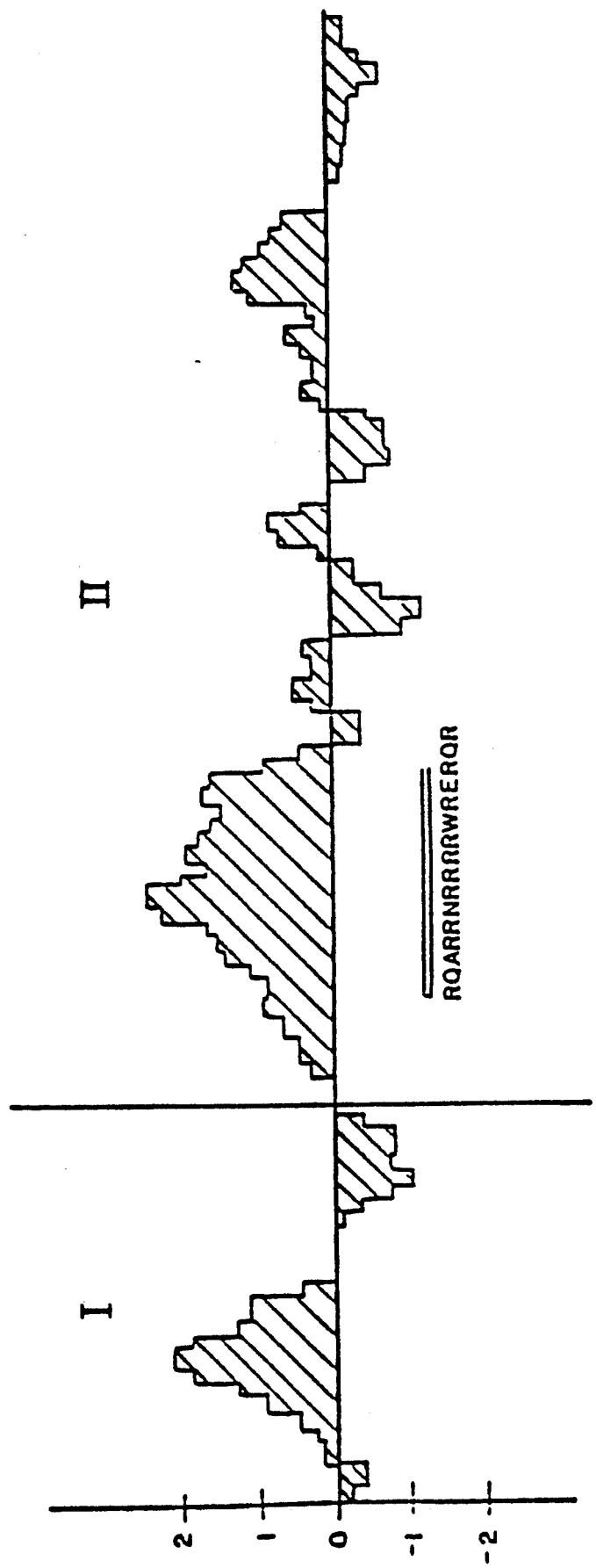
FIG. IC

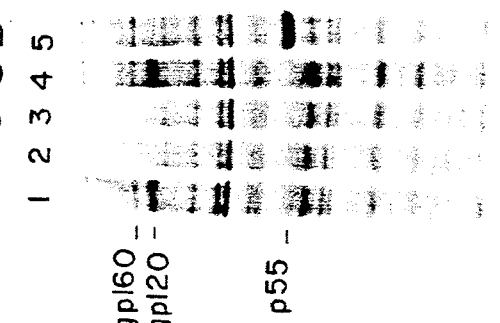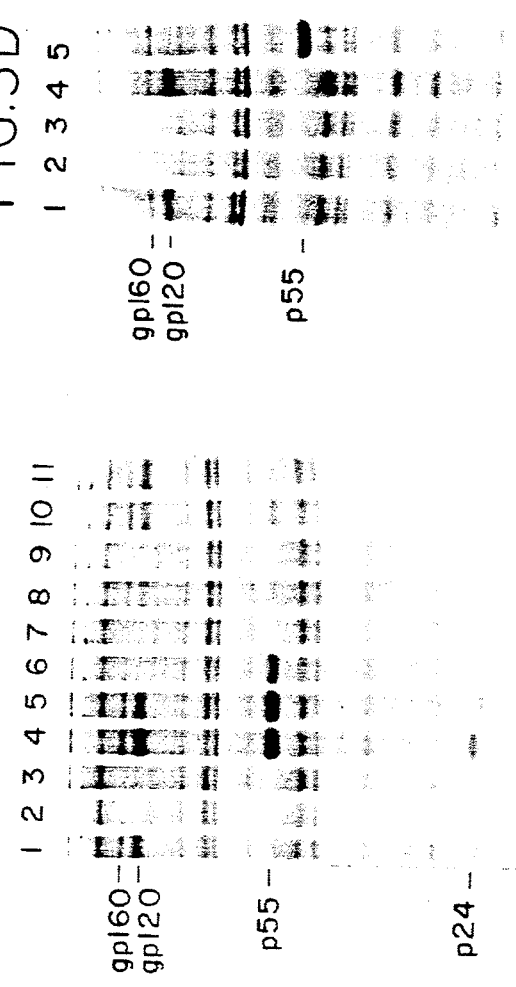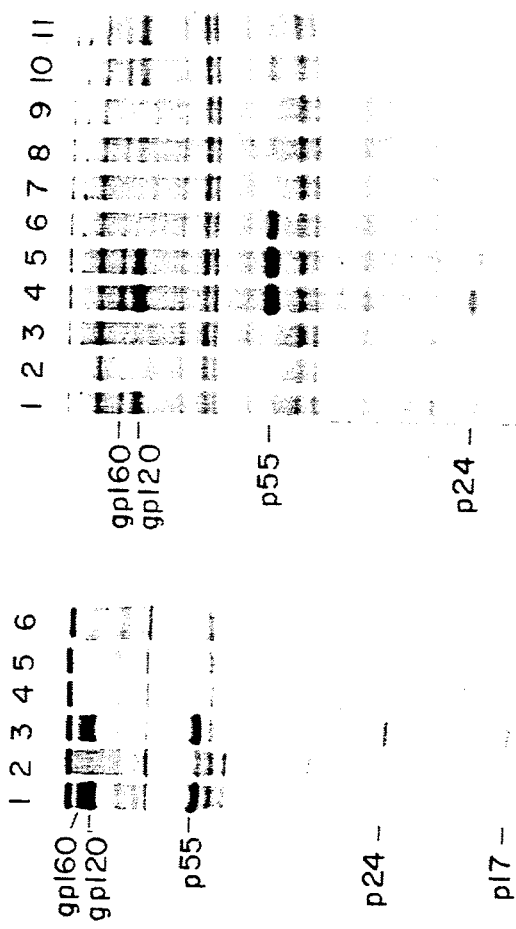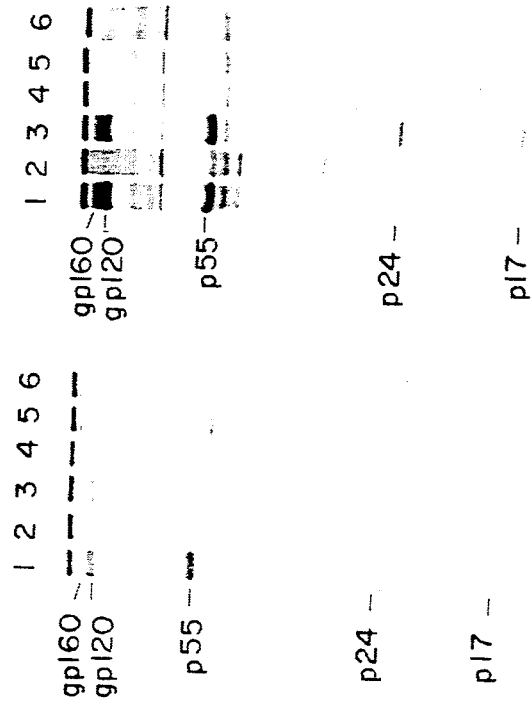

Induction of total bacterial proteins.
Lane 1: P_L art_III at 30°C.
Lane 2: P_L art_III at 42°C.
Lane 3: Clone 12.1 (out of frame plasmid) at 30°C.
Lane 4: Clone 12.1 (out of frame plasmid) at 42°C.

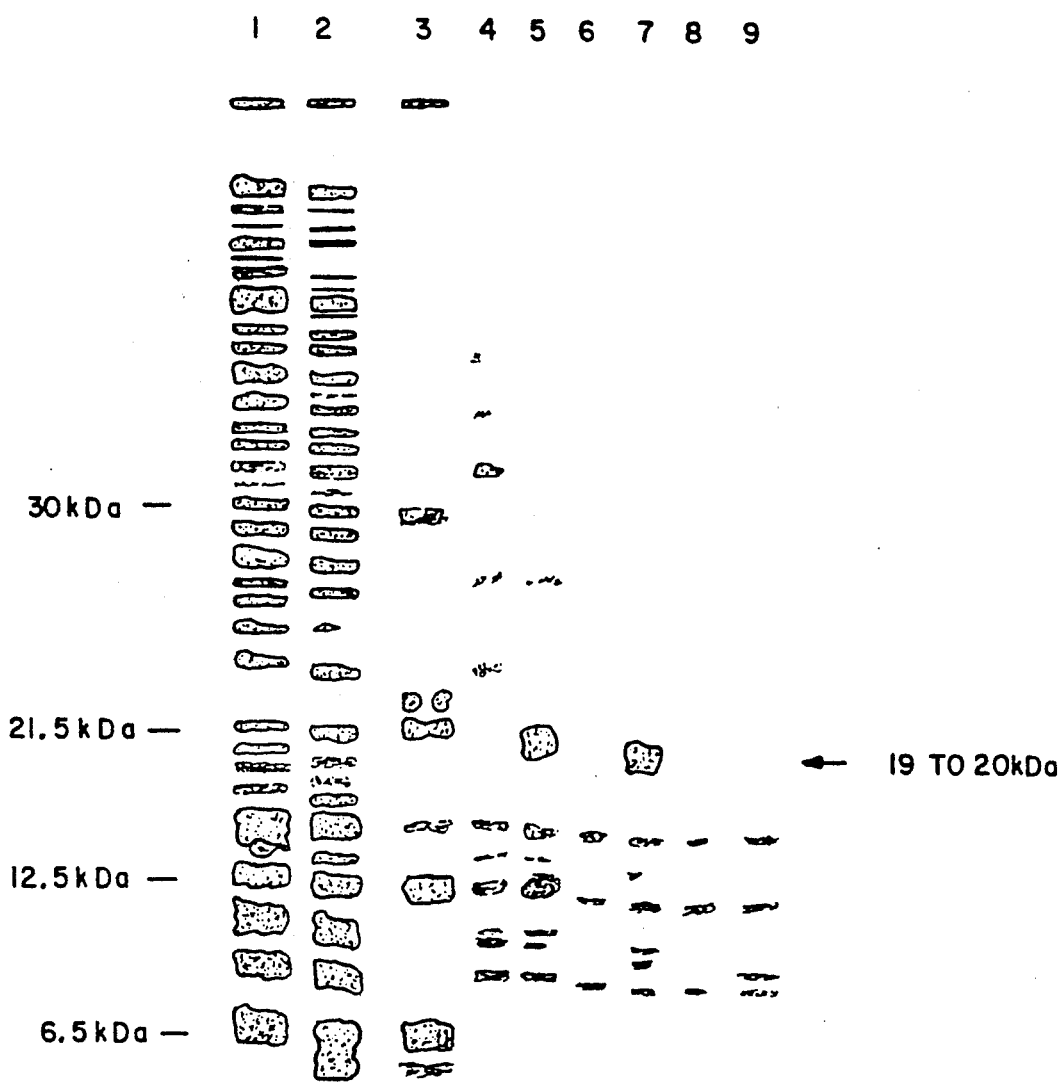

Lane 1: $P_L$ $art_{III}$ (clone 1.10) grown at 30°C.
Lane 2: $P_L$ $art_{III}$ (clone 1.10) grown at 42°C.
Lane 3: $^{14}C$-labeled markers purchased from Amersham.
Lane 4: Clone 1.10 grown at 30°C and immunoprecipitated with AIDS patient serum, RV119.
Lane 5: Clone 1.10 grown at 42°C and immunoprecipitated with RV119.
Lane 6: Clone 6.1 grown at 30°C and precipitated with RV119.
Lane 7: Clone 6.1 grown at 42°C and precipitated with RV119.
Lanes 8 and 9: Clone 12.1 (out of frame) precipitated with RV119, grown at 30°C or 42°C respectively.

FIG. 7B

ART (REV) PROTEIN OF HUMAN T-CELL LEUKEMIA VIRUS

This is a continuation of copending application Ser. No. 07/538,189 filed on Jun. 14, 1990, now abandoned, which is a divisional of Ser. No. 06/865,151, filed on May 20, 1986, now U.S. Pat. No. 4,935,372.

The present invention is directed to the use of vectors, transformants and cell lines containing the art gene now known as the rev gene, and the use of the art gene product for expression, diagnostic and therapeutic means. More particularly, the art gene product can be used to regulate the rate of expression of heterologous gene products.

Considerable effort has been spent over the years in attempting to understand the mode of action of viruses, particularly that of retroviruses. Questions for which answers have been sought include the reasons that certain of these viruses preferentially infect and/or replicate in certain types of cells as opposed to other types of cells and how the virus regulates its life cycle.

The Acquired Immune Deficiency Syndrome (AIDS), and AIDS-related complex have been the subject of intensive scientific research and public concern. Human T-Cell leukemia virus III (HTLV-III/LAV) renamed Human Immunodeficiency Virus (HIV) is the etiological agent of the acquired immune deficiency disease, AIDS-related complex and other virus-related disorders including degeneration of the central nervous system, lymphoid interstital pneumonitis (LIP) an increased incidence of Kaposi's sarcoma, B-cell lymphoma of a Burkitt's type, Hodgkin's lymphoma and thrombocytopenic purpera, collectively called HTLV-III/LAV related disorders [F. Barre'-Sinoussi et al., *Science* 200:868(1983); R. C. Gallo et al., ibid., 224:500 (1984); J. Schupback et al., ibid.: 503; M. G. Sarngadharan et al., ibid.: 506; J. A. Levy et al., ibid.: 225,840 (1984); D. Klatzmann et al., *Nature* (London) 313:767 (1984); M. Gottlieb et al., *New England J. Med.* 305:1425 (1981); H. Masur et al., ibid.:1431 F. Siegal et al., ibid.: 1439; H. Lane et al., ibid.:309,453 (1983); J. Ziegler et al., ibid.:311,565 (1984); G. Shaw et al., *Science* 227:177 (1985). D. Klatzman et al., *Science* 225:54 (1984); M. Seligman et al., *New England J. Med.* 311:1286 (1984)] AIDS is clinically typified by depletion of T-Cells of the T4+(helper) subset, a phenomena reflected by cytotoxicity of the virus for T4+ cells in vitro. Large scale production of the virus was made possible by the development of T4+ cell lines that were susceptible to virus infection but that were partially resistant to its cytopathic effects [M. Popovic et al., *Science* 224:497 (1984).]

The HTLV-III genome, like that of other retroviruses, contains three open reading frames encoding the capsid proteins (the gag gene), the envelope proteins (the env gene), and non-structural proteins necessary for replication (the pol gene) [Ratner, L. et al. *Nature* 313:227-284 (1985); Wain-Hobson, S., et al. *Cell* 40:9-19 (1985); Sanchez-Pescador, R. et al. *Science* 227:484-451 (1985); Muesing, M. A. et al., *Nature* 313:450-458 (1985); Robey, W. G. et al., *Science* 228:593-596 (1985); Veronese, F. et al., *Science* 229:1402-1405 (1985); Kitchen, L. et al., *Nature* 312:367-370 (1984); Schupbach, J. et al., *Science* 228: 503-505 (1984); and Allan, J. S. et al., *Science* 228:1091-1093 (1985)].

This genome also contains other open reading frames that encode at least three additional proteins not common to most retroviruses [Ratner L. et al., *Nature*, supra; Wain-Hobson, S. et al., *Cell* supra, Sanchez-Pescador, R. et al., *Science*, supra; Muesing, M. A. et al., *Nature* supra; Arya, S. et al., *Science* 229:69-74 (1985); Sodroski, J. et al., *Science* 229:74-77 (1985)]. Mutations in two of these open reading frames (the sor gene that encodes a 23 kD protein [Sodroski, J. et al., *Science* 231:1549-1553 (1986); Lee, T. H. et al., *Science* 231:1546-1549 (1986)] and the 3'orf gene that encodes a 27 kD protein, [Allan J. S. al., *Science* 230:810-812 (1985)]) do not eliminate the ability of the virus to replicate in and to kill T lymphocytes [Sodroski, J. et al., *Science* 231:supra]. The transactivator ($tat_{III}$) gene encodes a 14kD protein that post-transcriptionally stimulates HTLV-III long terminal repeat (LTR)-directed gene expression [U.S. patent application Ser. No. 806,263 filed Dec. 6, 1985; Rosen, C. A. et al., *Nature* 319:555-559 (1986); Sodroski, J. G., et al., *Science* 227:171-173 (1985); Arya, S. et al., *Science* 229, supra; and Sodroski, J. et al; *Science* 229 supra which are incorporated herein by reference] via an interaction with specific target sequences (called TAR) in the leader of viral messages [Rosen, C. A. et al., *Cell* 41:813-823 (1985)]. Mutations in the 5' portion of the first coding exon of the bipartite $tat_{III}$ gene destroy the ability of the virus to efficiently synthesize structural proteins and to replicate [U.S. patent application Ser. No. 806,263; Dayton, A. et al., *Cell* 44:941-947 (1986)]. These mutations can be complemented in trans in cell lines that constitutively express the $tat_{III}$ protein.

We previously discovered that it is possible to use the $tat_{III}$ gene and gene product to produce high levels of heterologous gene products. However, the production of certain gene products such as envelope protein can result in lysis of the cell. Consequently, the cell will die before producing large amounts of the desired protein.

Further, some cells possess proteolytic enzymes that break down heterologous protein and prevent the accumulation of large mounts of the heterologous protein.

It would be desirable to have a system where large amounts of "building blocks", the messenger RNA (mRNA) species corresponding to specific proteins, of a desired protein could be accumulated in a cell before production of that desired protein began and to then initiate production.

It would also be desirable to have additional means of identifying individuals possessing the HTLV-III/LAV virus.

Further, it would be advantageous to have a new mode of finding compounds that will prevent the infection, replication, propagation and spread from individual to individual of the cytopathic effects of the HTLV-III/LAV virus.

Still further, it would be beneficial to be able to produce non-lethal HTLV-III/LAV virus for both diagnostic and prophylatic purposes.

SUMMARY OF INVENTION

We have now discovered a gene and gene product that regulates the expression of the capsidal envelope genes of HTLV-III/LAV and that can be used to regulate the expression of heterologous (non-vital) genes as well. This art gene consists of two exons and can be used in creating nucleotide segments, vectors and cell lines. Additionally, we have found that this gene and gene product is necessary for the prolific replication of HTLV-III/LAV. Thus, we have found a new method for screening for compounds that inhibit the replication of HTLV-III. This method includes the steps of:
(1) transfecting a T-cell line with the HTLV-III art and env genes;
(2) thereafter, adding a preselected compound to the transformed cell line in increasing concentrations; and
(3) determining whether the compound effects the art function without being toxic to the cell.

A variation of this method involves the establishment of cell lines that contain the art sequences integrated into the cellular DNA and express art activity constitutively. Thereafter, steps 1 to 3 can be performed.

This gene and gene product can also be used in controlling the production of a desired heterologous gene product. This method includes the steps of:
(1) transfecting a preselected cell line with a vector containing a sufficient amount of the HTLV-III LTR to be responsive to a trans-activating protein upstream of a desired heterologous gene fused to a cis-acting negative sequence, capable of releasing a cis-acting inhibitory factor; and
(2) at a predetermined time contacting the cis-acting inhibitory factor with a sufficient amount of art gene product to repress the cis-acting inhibitory factor and permit expression of the desired heterologous gene product.

Further, this newly discovered protein of about 116 amino acid associated with HTLV-III/LAV, results in an additional parameter to use in diagnosis of the disease. Still further, the art gene and gene product can be used in AIDS therapy. For this purpose purified art protein or peptides derived therefrom, produced in bacteria, yeast or mammalian cells or synthesized chemically can be used to detect antibodies to the art protein in body fluids. Alternatively, antibodies raised to the art protein or peptides derived therefrom can be used to detect art protein in tissues or body fluids.

BRIEF DESCRIPTION OF THE FIGURES

FIG. 1B shows the DNA sequence of the two open reading frames that constitute the art gene and the predicted amino acid sequence of the art gene product.

FIG. 1C shows the hydrophilic (upper) - hydrophobic (lower) profile of the art gene product.

FIGS. 3A, 3B, 3C, and 3D show the complementation of mutations in HTLV-III proviruses by plasmids designed to express the art gene product.

FIGS. 7A and 7B show immunoprecipitates of the bacterially synthesized art protein using a patient antiserum.

DETAILED DESCRIPTION OF THE INVENTION

Figure 1A:
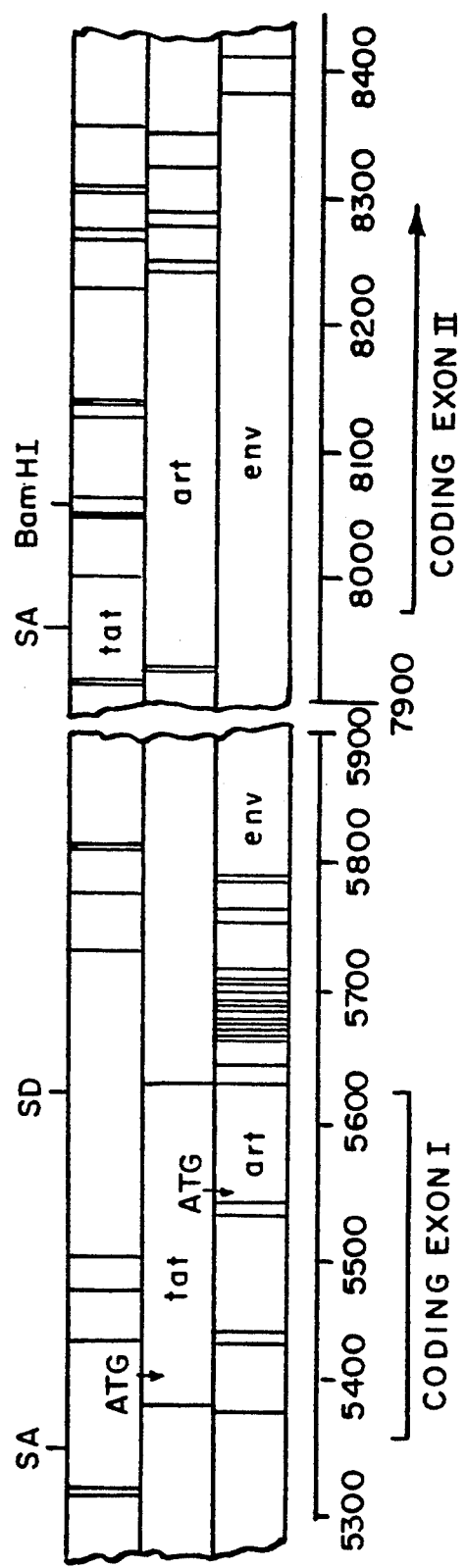
FIG. 1A shows the structure of the HTLV-III/LAV genome containing exons of the art gene.

We have now discovered a gene that produces a protein which in addition to the $tat_{III}$ gene product, is necessary for efficient HTLV-III gag and env protein synthesis. The coding exons of this gene use alternative reading frames of the first and second coding exons of the $tat_{III}$ gene (FIG. 1). Beginning at about a methionine codon at about nucleotide 5550, first coding exon of this gene extends to a known splice donor at about position 5625. The corresponding splice acceptor, located at about nucleotide 7956, precedes an in-frame open reading frame ending in a stop codon at about position 8227. The splicing events needed to produce this alternative reading frame product are the same as those used for the $tat_{III}$ gene and occur in the messenger RNA of HTLV-III infected cells.

The product of this alternative reading frame is about 116 amino acids long and contains highly basic hydrophilic stretches similar to those found in the $tat_{III}$ gene product and in nucleic acid-binding proteins.

The expression of HTLV-III structural genes is governed post-transcriptionally by the $tat_{III}$ product, which acts as a positive regulatory factor, and by the art product, which counteracts cis-acting negative-regulatory sequences located in or near the gag and env genes. Two possible roles for this complex regulatory scheme can be considered. HTLV-III is reported to establish a latent state of infection in T-cells that are not activated [Zagury et al. *Science* 231:850-853 (1986)]. Lack of $tat_{III}$ or art function would lead to a state of infection characterized by accumulation of viral RNA without synthesis of virus structural proteins. Rapid release form such a latent state could be achieved in the absence of new RNA synthesis if the $tat_{III}$ or art function were reconstituted. A dependence of $tat_{III}$ and art activity on the state of cell differentiation would explain the relationship between HTLV-III latency and T-cell activation.

Alternatively, post-transcriptional regulators may play a part in the lyric cycle of the virus. An early stage of infection characterized by accumulation of viral RNA but not of virion proteins might precede a late phase in which viral proteins toxic to T4 cells are produced. The switch from an early to a late stage of infection would reflect activation of either one or both of the $tat_{III}$ and art gene functions. Such an early-late switch would permit accumulation of the mRNAs for toxic virion components before such components themselves are produced. There is some evidence that modulated $tat_{III}$ activity may result in increased production of infectious virus. The yield of virus particles on lytic infection of the Jurkat cell line that constitutively produces high levels of the $tat_{III}$ gene is much lower than that observed on infection of the Jurkat cell line itself, despite the observation that the cytopathic effect of infection is accelerated in the Jurkat $tat_{III}$ cells. Premature cell death attributed to high constitutive levels of the $tat_{III}$ gene might explain the decreased virus titres. Temporal regulation of virus gene expression is important in the life cycle of other lytic viruses. The postulated roles of the $tat_{III}$ and art genes in the latent and lytic cycles of HTLV-III infection are not necessarily exclusive.

The flexible multi-tiered regulatory pathway linked to host cell differentiation and proliferation would-account for much of the variability observed in the disease consequent to HTLV-III infection [Seligman, M. et al., *N. Eng. J. Med.*, 311:1286–1292 (1984)]. Using such a multi-tiered regulatory pathway involving both positive and negative elements, should result in the production of high levels of a desired heterologous gene.

The necessity of the art gene product in addition to the $tat_{III}$ protein for efficient HTLV-III gag and env protein synthesis is demonstrated by preparing plasmids that delete parts of the two coding exons of the $tat_{III}$ gene with the result that, the ability of the virus to express gag and env proteins is dramatically reduced if not eliminated. Further, this attenuation of the virus is not the result of defective $tat_{III}$ gene product, because these mutations are not complemented by the addition of $tat_{III}$ gene products alone. Thus, it is clear that a second post-transcriptional control pathway is involved in HTLV-III expression.

Raji cells that have been transfected with plasmids containing these deletions (pΔ(8053-8474 and pFS8053) failed to express HTLV-III gag or env gene products, but did synthesize levels of the 14 kD $tat_{III}$ gene product in amounts comparable to that seen following transfection with the pHXBc2 plasmid. The $pHXBc_2$ expresses the env, gag and $tat_{III}$ gene products but does not synthesize a complete 3' orf gene product, as judged by radioimmunopercipitation. Thus, mutations at or near nucleotide position 8053 attenuate the ability of the provirus to synthesize gag and env protein, but do not affect the synthesis of the $tat_{III}$ protein. This is further shown in FIG. 2, which shows that proviruses containing mutations in the 3' portion of the env gene are able to stimulate HTLV-III LTR directed gene expression to approximately the same level as is observed in the intact pHXBc2 provirus. Thus, mutations that effect gag and env gene protein expression do not significantly effect $tat_{III}$ gene expression.

Significantly, plasmids which express the art gene product complement the defect of the delection mutants and result in the synthesis of the gag and env gene product. HTLV-III LTR sequences from −167 to +80 were placed at various positions with respect to the putative initiation codon for the art gene reading frame. Vital protein expression was assessed at 48 hours following transfection.

FIG. 3 illustrates that placement of the HTLV-III LTR 54 nucleotides 5' to the art ACG codon (and downstream of the $tat_{III}$ initiation codon) results in a plasmid (pEx5496) that provides in trans a function required for gag expression by one of the mutant plasmids (pFS8053). The gp160/120 env gene proteins are produced by the pEx5496 plasmid itself upon transfection into Jurkat-$tat_{III}$ cells. The ability of the pEx5496 plasmid to complement the pFS8053 mutation and to synthesize envelope proteins is eliminated by a frame shift mutation within the alternative reading frame (plasmid pEx5496FS). Plasmids in which the HTLV-III LTR is located 3 to the art ATG codon do not complement the pFS8053 mutations and also do not synthesize env gene products (See plasmids pEx5607 and pEx5702 in FIG. 4). In contrast, deletions within the env or 3'orf genes of plasmid pEx5496 do not eliminate the ability to activate gag gene expression by the pFS8053 plasmid (See plasmid pEx5496-Δ env and pEX(5496-8474) (FIGS. 3 and 4). Additionally, HTLV-III gag gene expression directed by the pΔ(8053-8474) plasmid can also be activated by the pEx5496 plasmid. This shows that plasmids capable of expressing art gene products can activate in trans gag gene expression by proviruses containing mutations that prevent expression of the art gene product.

We have further found that gag gene expression by the pFS8053 plasmid can be activated in Jurkat-$tat_{III}$ cells by a plasmid that contains the HTLV-III sequence located 5' to the initiation codon the $tat_{III}$ gene. The pEx5365 plasmid produces functional $tat_{III}$ activity, as well as providing in trans the functions required for gag gene expression (See FIG. 3). However, the extent of gag gene expression observed in this experiment was less than that observed in the experiments in which the pEx5496 plasmid was used.

Plasmids designed to express the art gene product, but not the env gene were tested for the ability to allow env gene production by HTLV-III proviruses containing mutations for the art gene. The plasmid pEx5496-Δenv contains a deletion-frameshift mutation in the portion of the env gene encoding the exterior glycoprotein, gp120. FIG. 3 illustrates that the pEx5496Δenv plasmid does not yield detectable levels of the env (ATCC 67135) protein upon transfection into Jurkat-$tat_{III}$ cells. Co-transfection of this plasmid into Jurkat-$tat_{III}$ cells with the pΔ(5365-5551) plasmid allows the latter plasmid to produce both gag and env proteins (See FIG. 3). No vital protein could be detected in Jurkat-$tat_{III}$ cells transfected either with the pΔ(5365-5551) plasmid alone or with the pΔ(5365-5551) and pEx5496FS plasmids. The pEx5496Δenv plasmid also activates this synthesis of the gp160/120 env products by the pEx5496FS and pEx5702 plasmids. No env gene products were detected upon transfection of Jurkat-$tat_{III}$ cells with the pEx5496FS and pEx5702 plasmids alone. This demonstrates that the inability of these plasmids to synthesize envelope protein is due to disruption of the art gene, rather than of cis-acting sequences required to produce envelope protein. This illustrates that a product expressed by the alternative reading frame, the art gene product, has a trans-activating function with respect to env gene expression and/or gag gene expression directed by proviruses mutated in the art gene.

Although, not wishing to be bound by theory, it is our belief that there is a cis-acting negative regulatory sequence present on viral messages encoding gag and env gene products which the art gene product depresses. This sequence results in a cis-acting inhibitory factor which prevents the expression of the env and gag gene products. We have previously found that the $tat_{III}$ gene product alone is sufficient to stimulate HTLV-III LTR sequences (−167 to +80) to direct high level synthesis of heterologous gene products such as bacterial chloramphenicol acetyltransferase and murine dihydrofolate reductase [(See U.S. Pat. No. 806,263 filed Dec. 6, 1985; Rosen, C. A., *Nature*, supra, Sodroski, J. G., et al., *Science*227:171-173 (1985)]. However, plasmids containing these same HTLV-III LTR sequences located 5' to the HTLV-III env gene (pEx5496FS or pEx5702) yield no detectable envelope protein in the absence of the art gene product, even in the presence of an active $tat_{III}$ gene product. It is only after this art gene product is supplied in trans do the levels of envelope production by the plasmids approximate those of the heterologous genes under the control of the HTLV-III LTR in Jurkat-tat$_{III}$ cells. These observations indicate that sequences in the pEx5496FS and pEx5702 plasmids 3' to +80 inhibit env gene expression, and that such inhibition can be relieved by the art gene trans-activating function. The requirement for this second transactivator for gag gene expression suggests that gag gene messages also contain repressor sequences in addition to those found in env gene messages. It is for the above reason that we have chosen the name art for the gene that encodes the second transactivator, standing for anti-repressor transactivator, consistent with the proposed role of this gene in negating the function of cis-acting repressor sequences present on vital messages encoding the HTLV-III structural proteins.

Figure 8:
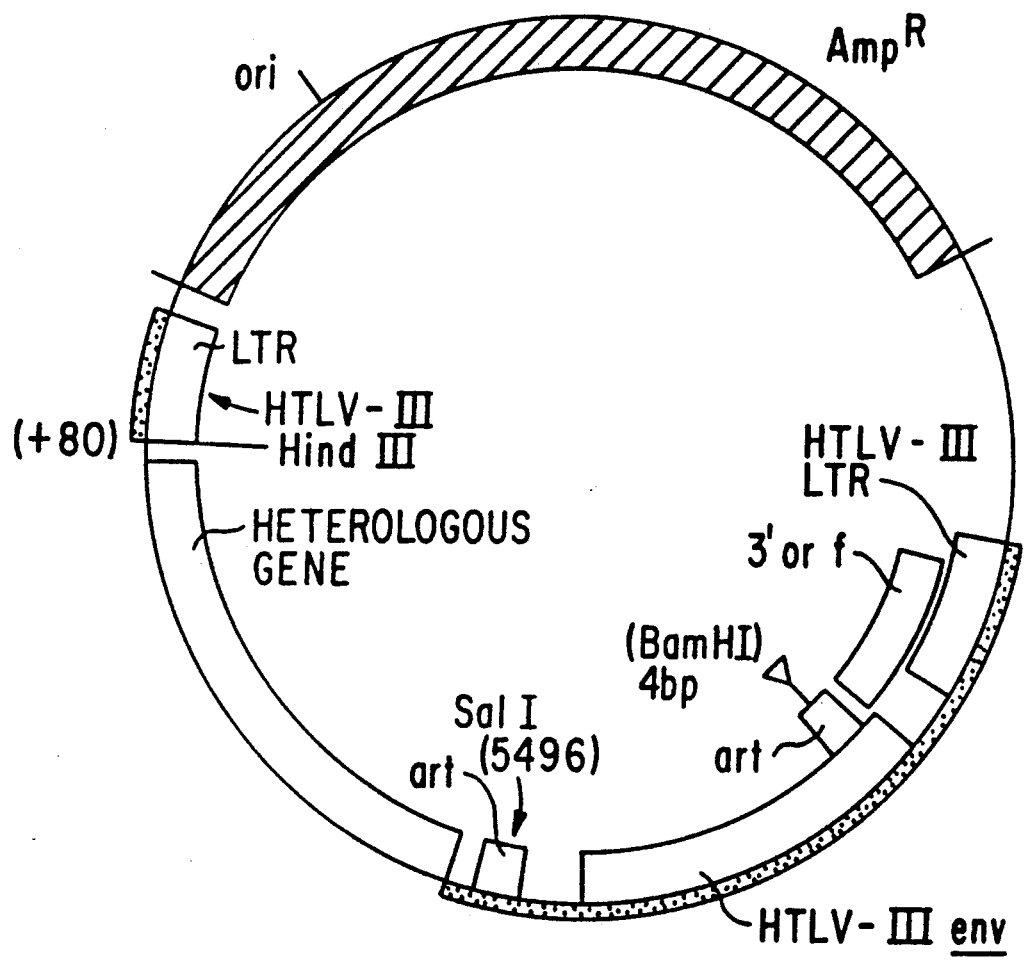
FIG. 8 shows a plasmid in which a nonvital (heterologous) gene, in this instance chloramphenicol acetyltransferase (CAT), is negatively regulated by cis-acting negative regulatory sequences present in the 3' terminal portion of the HTLV-III genome.

To test for the presence of a specific repressor sequence in vital genome the following recombinant plasmid was constructed (See FIG. 8). The bacterial chloramphenicol acetyltransferase (CAT) gene under control of the HTLV-III LTR was deleted of its polyadenylation signals and was joined to the 3' end of the HTLV-III genome. Following transfection of cells with this plasmid DNA CAT activity is virtually undetectable. However, co-transfection with an art expressor plasmid relieves repression and CAT activity is increased. These experiments demonstrate that the HTLV-III genome contains a repressor sequence that can be linked heterologous genes in order to control their activity. FIG. 8 illustrates as described above that art gene activity can relieve the negative effect of the HTLV-III cis-acting negative regulatory sequences. The sequences used for transcription initiation are derived from the HTLV-III LTR in this experiment and there may be a specific interaction between the HTLV-III LTR sequences and sequences in the gag and pol genes, respectively, required for the negative regulatory effect specifically relieved by art functions.

Detectable levels of the tat$_{III}$ gene but not of the gag and env gene products are synthesized by proviral mutants defective for the art function. The influences that inhibit gag and env gene products do not affect tat$_{III}$ gene expression. It is known that sequences encompassing the entire gag gene and most of the env gene are removed by splicing from the tat$_{III}$ messenger RNA [Muesing, M. A. et al., Nature 313, supra, Arya, S., Science 229, supra, Sodroski, Science 229, supra]. Removal of art-responsive cis-acting repressing sequences located in the regions spliced out of tat$_{III}$ messages, explain the independence of tat$_{III}$ expression from the requirement from the art product. The art product should also be independent of such a negative regulatory sequence as it is synthesized from messages that also lack these gag and env sequences. Heterogenity observed in the non-coding leader sequences of potential. tat$_{III}$ and art messages could determine ATG usage, in effect, modulating relative levels of tat$_{III}$ and art proteins.

We have now found a new process for screening for a compound that will mitigate the cytopathic effects of the HTLV-III/LAV virus. This process involves screening for a drug that will inactivate the art gene product. As discussed above, we now how that for the HTLV-III/LAV virus to express the capsidal envelope proteins at any significant levels, the art gene product is necessary. Because the envelope structural protein is necessary for the replication of the virus, by inactivating the art gene product and consequently preventing the replication of the envelope protein, it will be possible to mitigate, if not completely eliminate, the growth and the cytopathic effects of the virus.

The envelope protein kills T-cells in a very specific way. This protein hooks onto the T4 receptor of T4 cells and fuses the cells together. Thereafter, the fused cells die. Thus, by introducing a vector containing art gene and the env gene under the control of an HTLV-III LTR into a T-cell line, one can assay for a compound that inactivates the art gene and consequently prevents expression of the envelope gene product and thus, stops the fusion. Preferably T-cells that are particularly sensitive to the cytopathic effects of the envelope protein are used. More preferably, T4 cells would be used.

Although, any T4 cells can be used, preferably cell lines derived from HUT 78 cells, C8161 cells and Jurkat cells are used. More preferably, tat$_{III}$ cell lines are used, as disclosed in U.S. patent application No. 806,263. Most preferably, tat$_{III}$ cell lines derived from C8161 cells are used.

For example, cells of the C8166 T4+ lymphocyte line may be chosen as recepients for the assay because this line expresses markers typical of activated T-cells and is exquisitely sensitive to HTLV-III infection and cytopathicity. Just before the C8166 cells show their maximum HTLV-III specific, positive membrane fluorescence and extracellular reverse transcriptase (RT) activity, cytopathic changes occur that include syncytia formation, cellular enlargement, and extrusion of cell membranes. The number of viable cells decrease rapidly thereafter. No such changes occurred in C8166 cultures transfected with vectors that will not express the HTLV-III viral env gene.

Preferably, the cell lines will also contain a marker that is released upon the cell's death. This marker can be used to determine the cytopathic effect of the tested material. Thus, when a cell dies, the marker is released into the culture medium resulting in a reaction with the medium that is visually observed. Such markers can be readily selected by one of ordinary skill in the field and include, for example, chromium.

The assay system comprises transfecting a T4 cell line with the above-described art-env vector. Thereafter, a compound is added to the cells that would be expected to inactivate the art gene product in increasing dosages. Because the introduction of this vector would normally be cytopathic to the cell, whether or not the compound inactivates the art gene product is determined, merely by looking at whether or not the transfected cells died.

Typically, after transfection with these vectors, the cells will show cytopathic changes. Usually, six days after transfection, there is a dramatic decrease in the viability of the culture. Extracellular RT activity is detected in cell-free supernatants of such cultures. The cells demonstrate membrane fluorescence and die. Generally, this will occur within two weeks after transfection. Consequently, if the cell does not die, it can be assumed that the drug was effective in inactivating the art gene product. Further, if the compound being tested is cytopathic to the drug, it will kill the cell and release the marker in the cell. As an added control, one would preferably run parallel experiments with T4 cells that are mock-transfected. Such cell lines could not be killed by expression of the envelope protein, and one would readily be able to determine whether or not the compound being tested, and/or the concentration at which it is being tested is detrimental to the viability of a cell.

Preferably the transfection occurs by cocultivation of the T4 cell cultures with an art cell line. This cell line would be prepared by transfecting, for example, a B-lymphocyte cell line, such as Raji cells. The ability of these art cells to constitutively express the HTLV-III art and env products can be readily determined prior to cocultivation by techniques well known in the art. Preferably, this cell line would also be able to express the tat$_{III}$ protein. It is possible to establish stable cell lines that express these genes and therefore, one has an easy and reliable method to transfect T4 cells each time one wants to test a new drug. For example, one could simply treat these art cells with mitomycin C and cultivate the cells with T4 cells, such as C8166 cells. The ratio of art cells to T4 cells can vary widely. Typically, the ratio ranges from 5 to 1 through 1 to 5, preferably, the ratio is about 1 to 3. Thereafter, the T4 cells that have been cocultivated with the art cells will show cytopathic changes, indistinguishable from those observed after transfection of the T4 cells.

Preferred cell lines that express the art gene product include Raji, Hela, NIH 3T3, Jurkat, T-cell, B-cell and CHO.

It is preferable to screen compounds that prevent the interaction of the art protein with the sequences responsive to the art protein in the HTLV-III LTR or prevent the ability of the art protein to trans-activate the HTLV-III LTR. HTLV-III structural gene expression is governed post-transcriptionally by the tat$_{III}$ product that acts as a positive regulatory factor and by the art product that counteracts a cis-acting inhibitory factor resulting from cis-acting negative sequences located in or near the gag and env genes. Consequently, using compounds that inhibit translation, such as substances that affect the formation of translational initiation complexes or alter the bonding of ribosomes to the viral mRNA is most preferable.

Examples of compounds that can be used in this screening process include competitors, compounds that inhibit translation and compounds that alter the binding ability of a compound. Compounds such as those described in the *Physicians' Desk Reference,* 38th ed. Medical Economics Co., Droden, N.J. (1984), which can be used in the present screening process can be readily determined by the person of ordinary skill in the art based upon the above disclosure.

A preferred group of competitors would be mutant art proteins that would retain their ability to bind to nucleic acid but are deficient in overcoming the inhibitory affect of the cis-acting factor. Such proteins should serve as efficient competitors for functional art proteins. Random mutagenesis by, for example, chemical modification can be used to generate large numbers of art mutants without a specified target region. In one embodiment, one would use the first coding exon of art which can be isolated using convenient restriction endonuclease sites. This region will be cloned into the replicative form of phage M13.

Single stranded M13 containing the art insert in either-orientation is mutagenized using methoxyamine. This can generate single and double nucleotide substitutions at a frequency of greater than 50% [(Kadonaga and Knowles, *Nucl. Acids Res.,* 13:1733 (1985)]. The single stranded DNA of a clone in one orientation is annealed to that of a clone in another orientation so that a double stranded insert is reconstituted. The chemically modified inserts are removed from vector M13 DNA by restriction digestion and recloned into cut alkaline-phosphatase treated M13 replicative form DNA. Clones containing inserts are identified by the colorless plaques generated when the insert disrupts the beta-galactosidase gene present in the M13 vector. The insert fragment can then be sequenced using the dideoxy method of Sanger et al., *PNAS,* 74:5463: (1977)

Following generation and sequencing of art mutants in M13 by the methods described above, the insert fragments are recloned into an HTLV-III expression vector containing HTLV-III LTR, and transfected into eukaryotic cells. The activity of the mutant art proteins will be determined by testing their ability to activate the HTLV-III LTR directed HTLV-III gag or env gene protein synthesis in cells that also contain the HTLV-III provirus intact except for a mutation that inactivates the art gene for example the provirus on plasmid pFS8053 in co-transfection assays. Using T4 cells transfected with gag and env and, preferably also the tat$_{III}$ gene, but not an unmodified wild type art gene, as many as 100 plasmid clones can be tested for activity in the period of one week. Moreover, mutations that increase or decrease the trans-activating ability of the mutant art gene product can be detected in a quantitative manner by looking an the degree and speed of cell death.

Those mutants that are no longer able to trans-activate will be tested in the above-described screening process. If a mutant art protein that can effectively compete with the active form is found then the mutant art gene will be subcloned into the retroviral vector.

Art protein may also be used to test for the presence of HTLV-III/LAV. For example, art protein may be purified by reversed-phase HPLC and used to elicit antibodies. This protein is then used to immunize rabbits using techniques well-known to the person of ordinary skill in the field. Rabbit antiserum to art protein is then used in an immunoprecipitation analysis in potentially HTLV-III/LAV infected cells. Cells are metabolically labelled and the cell extract is immunoprecipitated with the rabbit antiserum. Western blot assay is typically used [See Samuel, D. P. et al., *Science* 226:1094 (1984)]. Antigen-antibody complexes may be detected by known techniques, for example, using a radioactive labeled protein. FIG. 7 indicates that the art protein is approximately 19 to 20 kilodaltons in molecular weight and elicits an immogenic response in infected patients. The availability of bacterially produced art protein will make it possible to carry out serological studies on the prevalance of antibodies during the disease course. Besides its use as a diagnostic reagent, purified art protein will make it possible to fully study its biochemical properties.

The vectors used in the present invention can be in the form of plasmids or viral vectors such as those described in PCT/US85/00986 filed May 24, 1984. For example, the defective retrovital vector pZIP-NEOSV(X)1 prepared as described by Cepko et al., supra contains Moloney murine leukemia virus LTR's, polyadenylation signals, sequences required for reverse transcription and for encapsidation of RNA, as well as the 5' and 3' splicing signals that normally produce subgenomic env gene messenger RNA. This vector also contains the bacterial gene for neomycin resistance (neo) which confers a dominant selectable resistance to the antibiotic G418 in eukaryotic cells (Southern, P. J. et el., *J. Mol. Appl. Genet.* 1:327–341 (1982)) so that art transfected cells can readily be identified. Preferably, the vector can contain any element such as antibiotic resistance, which will permit easy detection of a transfected cell.

The HTLV-III/LAV art gene used herein was obtained from infectious proviral clone HXBc2 and encodes an HTLV-III/LAV associated trans-acting factor, although it can readily be obtained from other HTLV-III/LAV sources.

Cell lines which stably express the art gene can be created by infection using a vector containing the art gene.

DNA is introduced into the psi/2 (ecotropic) and psi AM (amphotropic) cell lines by the calcium phosphate coprecipitation method (Wiglet et el., *Cell* 16:777-785 (1979). These lines constitutively produce the murine leukemia virus proteins but cannot package the vital transcripts (Cone, at el., *P.N.A.S* 81:6349-6353 (1984): Mann, et el., *Cell* 33:153-159 (1983)). Two days following transfection, cells are selected with the antibiotic G418 (400 g/ml for fibroblast lines and 700 g/ml for lymphocytes). G418 resistant clones are evident in 7 to 10 days. Insertion of the art exons does not interfere with splicing events required for transcription of the neo genes. G418-resistant psi 2 and psi AM clones are isolated and the virus from clones producing greater than $10^3$ infectious units per ml are used to infect the test cells. (King et al., *Science* 228:554-558 (1985)). Cells resistance to G418 are observed subsequent to infection of the cell lines tested.

By substituting the Moloney LTR with other modified LTR's a tissue specific expression vector can be obtained. The vectors are constructed using a tissue specific enhancer(s) operatively positioned in the same sequence with a heterologous DNA segment corresponding to the polypeptide of interest, as well as a stop codon and polyadenylation sequence downstream (3') from that gene. The vector should also contain a replication origin.

The vector contains at least the segment of an enhancer which determines the tissue specificity of that enhancer, hereinafter referred to as the "tissue specificity determinant." The vector preferably contains a complete viral enhancer, rather than just the tissue specific determinant from such an enhancer and preferably the tissue specific determinant is part of the complete enhancers.

The promoter contained in the vector can be any of the known promoters which function to permit expression of a desired product in host of choice. Preferably the promoter is a vital promoter from the same class of virus as the enhancer. The preferred class of virus is reprovirus, and the preferred viruses for use in conjunction with invention are the Akv, SL3-3, and Friend viruses.

The term "tissue specific" as used in this disclosure and claims, means that the vector operates to produce a greater amount of desired product in the targeted tissue than it does in other tissues under normal culture conditions. Tissue specific vectors may produce 1.5 to 1,000 or more times as much expression product in the target tissue as in other tissues. These tissue specific expression vectors are more fully described in PCT/US85/00986 which is incorporated by reference.

The tissue specific determinant can be homologous, meaning it came from the same virus as the promoter, or heterologous, in which case it is not from the same virus as the promoter. Heterologous tissue specific determinants can be excised from other viral systems, or can be synthesized using known techniques. Tissue specific determinants which are specific to the target tissue can be identified by assay techniques, where vectors encoding an indicator or marker compound, e.g., chloramphenicol acetyl transferase (CAT), an indicator which can be easily quantified as described below, to determine which vectors are effective in the tissue.

If desired, enhancer(s) from tissue specific vectors can be compared in DNA sequence to the enhancers which are not specific to the target tissue to determine the DNA sequence of the tissue specific determinant. Thereafter, at least the tissue specific determinant, preferably the entire enhancer, may be utilized in the desired vector containing the art gene and the resulting tissue specific vectors utilized to express this gene product in the tissue of choice.

Various cell lines can differ in their ability to take up and express the transfected art DNA. For example, Raji cells, HUT 78 cells, Jurkat cells, Hela cells and NIH 3T3 cells are useful. Human T-cells and B-cells, generally are very useful. Another useful method of achieving transfection with the art DNA is to use cells infected with either HTLV-I or HTLV-II.

The present invention also permits the development of a multi-tiered gene expression system. For example, by placing a desired heterologous gene under the control of the responsive sequence of an HTLV-III LTR and the cis-acting negative sequences that are located in or near either the gag or env gene, one can prevent the expression of the desired heterologous gene until the cis-acting inhibitory effect is "counter balanced" by the art gene product. The entire HTLV-III LTR region need not be used in the vector, the HTLV-III TAR +1 to +80 sequence in addition to functional promotor and enhancer sequences either of HTLV-III LTR origin or of heterologous origin (for example enhancer-promotor of other retroviruses, DNA viruses, or cellular genes) should be sufficient. The cis-acting negative sequences are obtained by fusing the cis-acting negative sequences of the env and/or gag gene to the desired heterologous gene and placing this downstream of at least the HTLV-III TAR sequence. The cis-acting negative sequence can be obtained by using the HTLV-III gag gene sequence. Alternatively, the cis-acting negative sequence from the env gene could be used instead of, or in addition to, the sequences from the gag gene. Most preferably, one would Just use a nucleotide sequences coding for the cis-acting inhibitory region.

One could use an expression vector, of the type described above, containing, for example, an HTLV-III LTR sequence, downstream of this sequence is the desired heterologous gene lacking polyadenylation sequences. This region would be limited to the HTLV-III sequences containing sufficient nucleotides of the HTLV-III gag gene and/or the HTLV-III env gene to convey the cis-acting inhibitory effect, but excluding sufficient nucleotides of the art gene to express function gene product. Preferably, sufficient nucleotides of the $tat_{III}$ gene to express functional $tat_{III}$ gene product and/or vital polyadenylation sequences are also present. Such a vector can readily be constructed by one of ordinary skill in the art, (See for example, FIG. 8).

Thereafter, this vector would be used to transfect a cell. If the vector used does not contain the $tat_{III}$ sequence, then preferably, this cell would also be contacted with $tat_{III}$ gene product. This contacting with a $tat_{III}$ gene product can be accomplished by a variety of methods. For example, this vector could be used on a $tat_{III}$ cell line, or one could subsequently transfect the transformed cis-negative sequence containing cell with a tat$_{III}$ gene or adding operable tat$_{III}$ gene product to this cell. As a result of the presence of the cis-acting sequences, one would obtain large quantities of mRNA for the desired heterologous gene, but the heterologous gene would not be expressed until the cell was exposed to a sufficient amount of the art gene product to repress the cis-acting inhibitory factor.

This exposure to the art gene product could be accomplished by a variety of mechanisms. For example, one could add the art gene product directly to the cell's culture medium at a desired preselected time. Alternatively, one could create art cell lines where the art gene product expression is under the control of a secondary factor. For example, one could develop a cell line where art gene production is temperature dependant. Thus, until the temperature is raised to a certain point, that cell would not produce sufficient amounts of art gene product to counteract the cis-acting inhibitory factor. When using such an art cell line, one would wait until a pre-determined time before raising the temperature of the cell. One could readily determine how long it takes a particular cell line with a given culture medium and at a given temperature to produce a specific amount of mRNA for the heterologous gene product.

Another method could have the art gene under the control of some chemical factor, which is affected by the addition of some compound, such as a hormone. These types of cell lines can be readily developed by one of ordinary skill in the art using standard techniques. For example, the art gene could be placed 3' to the mouse mammary tumor virus long terminal repeat or the metallothionein promoter, which are responsive to dexamethasone and heavy metals, respectively.

Alternatively, at a desired time, one could either transfect the cell with a vector containing the art gene or cocultivate the transfected cell with an art cell line. This will again result in the cells being exposed to the art gene product.

Upon exposure to the art gene product, in sufficient amounts, the inhibitory effect of the cis-acting negative sequence would be overcome and the desired protein would be expressed rapidly. Because high levels of mRNA have already been built up, before expression begins, one can readily obtain expression of the desired gene product in high levels in a short period of time. When this expression is carried out in the presence of tat$_{III}$ gene product, very high levels of protein production result. Thus, problems encountered with the expression of heterologous genes such as cell death or enzymatic attack on the heterologous protein can be minimized. For example, in the latter case one would know when the vast majority of the desired protein was being produced and could use known techniques to inactivate the enzyme even including killing the cell and then collecting the desired protein.

If a gag (and/or env)-desired heterologous gene product fusion protein is created, one can obtain the desired protein by cleaving the fusion polypeptide and separating the desired gene product from the other constituents by techniques well known to one of ordinary skill in the art, such as centrifugation, chromotography, etc.

When a fusion polypeptide, including the envelope gene is created, the transfected cell line is preferably a cell line other than a T-cell line. For example, a B-cell line would be most preferable.

This system also permits research regarding the effect of a single gene on a cell. By introducing into a cell, the desired gene to be studied under the control of the cis-acting inhibitory factor one can turn the gene "on" and "off" as desired by introducing the art protein.

This system can also be adapted for use in multicellular organisms, for example, with trangenic mice. One line of mice can be created containing the preselected gene to be studied under the control of the cis-acting negative sequences by using standard techniques. In this line of mice, the gene would be permanently shut off. Another transgenic line can be created that has the art gene and will express the art protein. These two lines of mice are then mated and the effects of the gene can be studied because the hybrid offsprings will contain both the preselected gene and the art gene.

The present invention can also be used to create a live attenuated vaccine. By using a provirus, in which the functional part of the art region is deleted, the virus, although capable of infecting the cells, is not able to express the envelope protein, and therefore, cannot cause the disease. Because of the small size of the two art exons, this attenuated virus used would closely resemble the complete virus.

The present invention is further illustrated by the following examples. These examples are provided to aid in understanding of the invention and are not to be construed as a limitation thereof.

EXAMPLE 1

Construction of Vector Used to Establish Art Cell Lines

The defective retroviral vector pZIPNEOSV(X) developed by Mulligan and coworkers [Cepko, et al., *Cell* 37:1053–1062 (1984)] was used to construct a vector for establishing stable art cell lines. This vector contains Moloney murine leukemia virus LTRs, polyadenylation signals, sequences required for reverse transcription and for encapsidation of RNA as well as the 3' and 5' splicing that normally produce subgenomic RNA. In addition, the vector contains the bacterial neomycin (neo) resistance genes that confers a dominant selectable resistance to the antibiotic G418 in eukaryotic cells [Southern and Berg, *J. Mol. Appl. Genet.* 1:327–341 (1982)]. The art gene of HTLV-III was obtained from infectious proviral clone HXBc2 and encodes the HTLV-III/LAV associated trans-acting factor (Arya et al., *Science* 229:69–73 (1985); Sodroski et al., *Science* 229:74–77 (1985); Sodroski, J. et al., *Science* 231:1546–1549 (1986); Fisher, et al., *Nature* 316, 262–265 (1985)].

Figure 4:
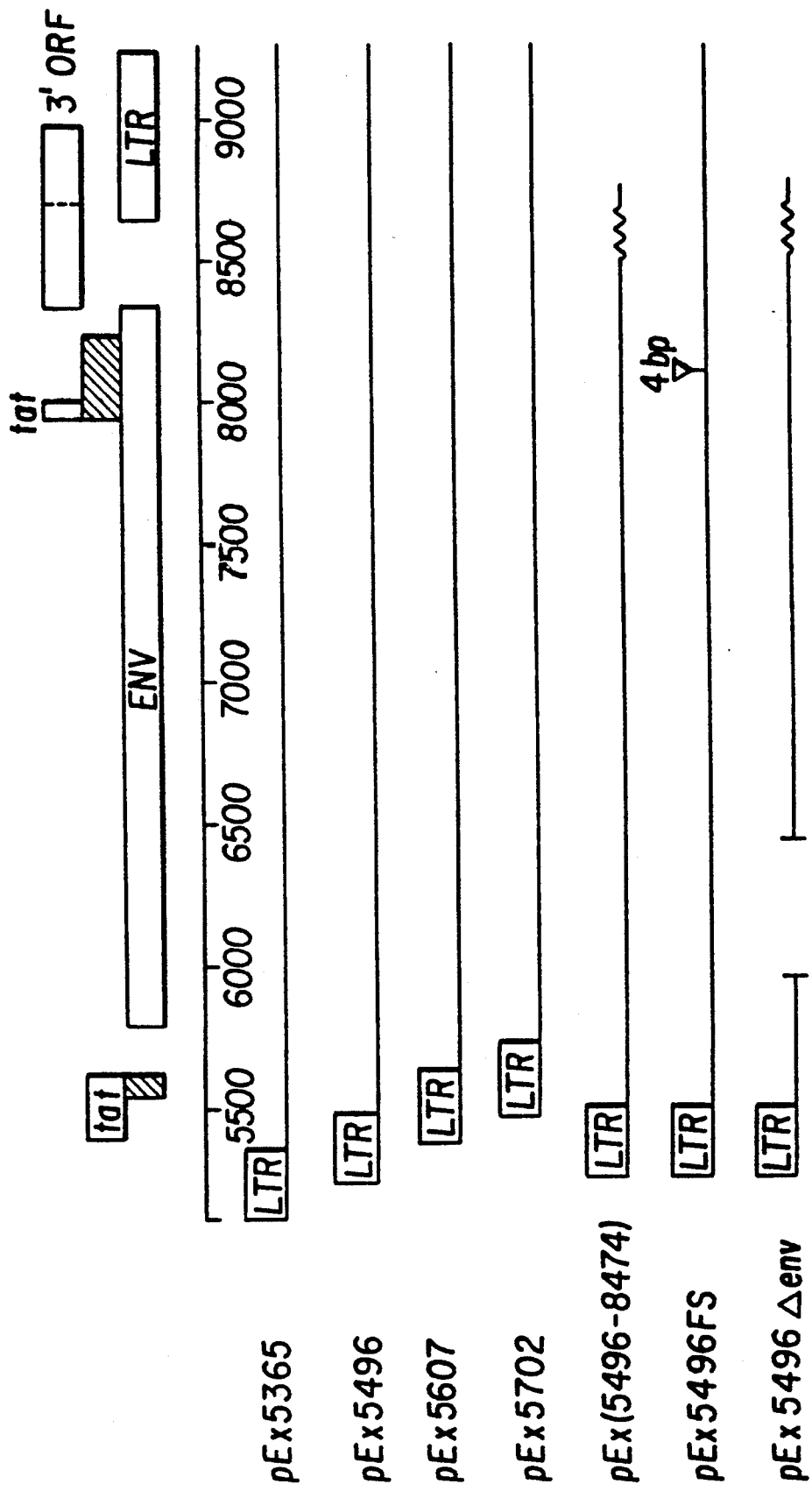
FIG. 4 is a schematic representation of plasmids containing the art gene.

In all plasmids prepared (See FIG. 4), HTLV-III LTR Sequences from −167 to +80 are positioned at the nucleotide denoted in the plasmid name. FIG. 4 shows the structure of the 3'half of the HTLV-III genome based upon the sequence of Rather et al., *Nature* 313, supra, including the positions of the env-gene, LTR, 3' orf gene, two tat$_{III}$ coding exons, the two art coding exons (here depicted as solid black boxes). The position of a stop codon in the 3' orf gene of the parental pHXBc2 used is denoted by a vertical broken line. The zig-zag lines represent signals for polyadenylation and splicing derived from the simian virus 40 early region [See Mulligan, R. C. et al., *Nature* 277:108–114 (1979)].

All plasmids were made by standard procedures using restriction and modification enzymes according to manufacturer's suggestions. For the proviral deletion mutants, the numerals in the plasmid name correspond to the endpoints of the deletion. These deletion mutants can readily be made by a person of ordinary skill in the art. The four nucleotide insertion (4 base pair) in plasmid pEx5496FS was constructed by treating a BamH1-digested provirus with the large fragment of DNA polymerase I in the presence of nucleotide triphosphates and religating prior to transfection of *E. coli*. The pEx5496Z env plasmid was constructed by digesting the pEx(5496-8474) plasmid with the enzyme Stu I, ligating to eight base pair Kpn I linkers, digesting to completion with Kpn I and ligating prior to *E. coli* transfection.

FIG. 1 shows the structure of the HTLV-III art gene end-product. The upper figure (1A) depicts the open reading frames in the HTLV-III genome based on the sequence of Ratnet et al., *Nature* 313, supra. The vertical lines represent the position of stop codons. The open reading frames for the $tat_{III}$ env and art are noted. The positions of known splice acceptors (SA) and donors (SD) (See, e.g. Muesing, M. A. et al. *Nature* 313 supra) as well as the BamH1 site used for mutagenesis (position 8053) are denoted. The putative initiator methionine codons for the $tat_{III}$ gene and art are delineated beneath the figure.

The middle figure (1B) shows the DNA sequence of the two open reading frames that constitute the art gene with the positions of the expected splice donor (SD) and acceptor (SA) sequences noted. The predicted amino acid sequence of the potential product of the open reading frame is provided beneath the DNA sequence. If this splice donor and acceptor are used, the amino acid sequence encoded by the sequence near the splice site would be LYQSNPPPNP.

The lower figure (1C) shows the hydrophilic (up) - hydrophobic (down) profile of the predicted arc product based on the program of Hopp and Woods [Hopp, T. P. et al., P.N.A.S. 78:3824-3825 (1981)]. Protein domains specified by the first coding exon (I) are separated by a vertical line from those specified by the second coding exon (II). The amino acid sequence of a strongly hydrophilic, basic domain is shown beneath the profile.

EXAMPLE 2

Transfection of Cell Lines with Art Vector

Jurkat-$tat_{III}$ cells were transfected by the DEAE-dextran procedure using ten micrograms of the proviral mutant to be complemented and ten micrograms of the plasmid to be tested for ability to complement the mutation. Forty-eight hours after transfection, cells were labelled with $^{35}S$-cysteine and cell lysates were immunoprecipitated using an AIDS patient serum RV119. [Lee. T. J. et el., *Proc. Natl. Acad. Sci. U.S.A.* 81:3856-3860 (1984)]. The positions of the gp160 and gp120 env proteins and the p55, p24, and p17 gag gene products are denoted. Transfected plasmids in FIG. 3A were pΔ(5365-5496) (lane 1), pEx5365 (lane 2), pEx5496 (lane 3), pEx5607 (lane 4), pEx5702 (lane 5) and pIIIβ-globin (lane 6). Transfected plasmids in FIG. 3B were pΔ(5365-5496) (lane 1), pFS8053 plus pEx5365 (lane 2), pFS8053 plus pEx5496(lane 3), pFS8053 plus pEx5607 (lane 4) pFS8053 plus pEx5702 (lane 5), and pFS8053 alone (lane 6). Transfected plasmids in FIG. 3C were pEx(5496-8474) (lane 1), pEx5496Δ env (lane 2), pEx5496FS (lane 3), pFS8053 plus pEx5496 (lane 4), pFS8053 plus pEx(5496-8474) (lane 5), pFS8053 plus pEx5496Δ env (lane 6), pFS8053 plus pEx5496FS (lane 7), pΔ(5365-5551) plus pEx5496 env (lane 8), pΔ(5365-5551) plus pEx5496FS (lane 9), pΔ(5365-5539) plus pEx5496Δ env (lane 10), and pΔ(5365-5539) plus pEx5496FS(lane 11). Transfected plasmids in FIG. 3D were pEx(5496-8474) (lane 1), pEx5496Δenv (lane 2), pEx5496FS (lane 3), pEx5496Δenv plus pEx5496FS (lane 4), and pEx5496Δenv plus pFS8053. The predicted env gene product synthesized by the pEx5496FS plasmid is 47 amino acids shorter than the wild type HTLV-III envelope due to the frameshift mutation.

EXAMPLE 3

Preparation of Deletion Mutants

All deletion mutant plasmids were made by standard procedures using restriction and modification enzymes according to manufacturer's suggestions. The 4 base pair (4 bp) insertion in the pFS8053 plasmid resulted from treating a BamH1-digested provirus with the large fragment of DNA polymerase I in the presence of nucleotide triphosphates and religating prior to transfection of *E. coli*.

Figure 2:
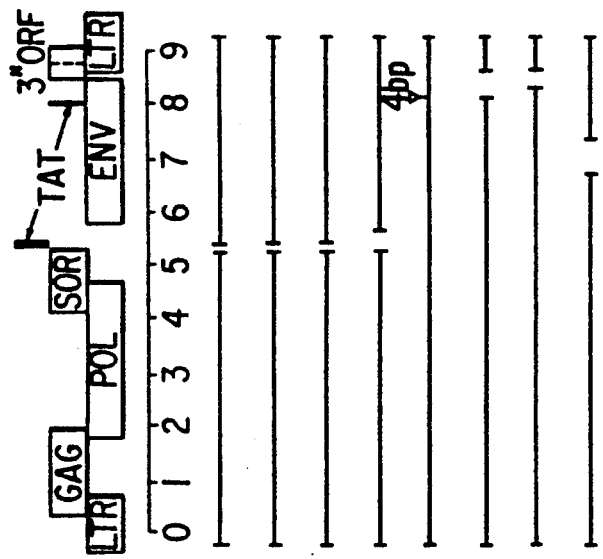
FIG. 2 shows the structure of HTLV-III proviral deletion mutants and illustrates the replicative potential of the proviral deletion mutants as indicated by transfection into Jurkat-$tat_{III}$ cells.

FIG. 2 shows the structure and properties of the HTLV-III proviral mutants. The complete HTLV-III provirus on plasmid pHXBc2 along with known genes is shown in the upper left FIG. (2A). [See Fisher, A. C. et al., *Nature* 316, supra]. The dark boxes represent the two coding exons of the $tat_{III}$ gene. The vertical broken line in the 3' orf gene represents a stop codon present in the pHXBc2 provirus [Sodroski, J. et al., *Science*, supra (1986). The scale beneath the viral genes represents kilobases. Numbers correspond to those by Ratner, where the RNA cap site is designated +1. For proviral deletion mutants, the numerals in the plasmid name correspond to the endpoints of the deletion.

Replicative potential of the proviruses was tested by transfection of CsCl-banded DNA into Jurkat-$tat_{III}$ cells [Rosen, C. A., et al., *J. Virology* 57:379-384 (1986)] using the DEAE-dextran technique [Queen et al., *Cell.* 33, supra]. The values in the MIF and CPE columns represent the number of days following transfection that greater than 95% HTLV-III-specific membrane immunofluorescence and greater than 95% cytopathicity, respectively, were noted in a typical experiment. These values were assessed as previously described by Sodroski,. J. et al. [*Science* (1986) supra]. The value ">30 days" indicates that not greater than 2 percent HTLV-III-related membrane immunofluorescence or cytopathic effect was observed in the cultures, even up to 30 days following transfection. Reverse transcriptase assays [See Rho, R. M. et al, Virology 112:335-342 (1981)] of cell supernatants in these cases did not rise above background during the observation period. ND-not done. (See FIG. 2B).

Assessment of Viral RNA production was performed as described below. Viral protein production was assessed by transfecting cells with 10 micrograms plasmid DNA using the DEAE-dextran procedure and labelling with $^{35}S$-cysteine at 48 to 72 hours post-transfection. Labelled cell lysates were precipitated with patient antisera (RV119 for Jurkat-$tat_{III}$ cells and 38-1 for Raji cells) and assessed for gag, env and $tat_{III}$ protein production on SDS-acrylamide gels [Lee, T. J. et al., *P.N.A.S.* 81:3856-3860 (1984)]. A positive (+) value indicates detectable gag (p55, p38, p24 and/or p17), env (gp160/120) or $tat_{III}$ (p14) bands, whereas a negative (−) value indicates no detectable level of these proteins above background.

Trans-activating ability (TA) was assessed by co-transfecting 10 micrograms of the proviral plasmid with 10 micrograms of plasmid pU3R-III, containing HTLV-III LTR sequences from −457 to +80 5' to the chloramphenicol acetyltransferase (CAT) gene, into Raji cells [Sodroski, J. et al., *Science* 225:381-384 (1984); Gorman, C. M. et al., *Mol. Cell. Biol* 2:1044–1051 (1982)]. Forty-eight hours after transfection, cell lysates were assayed for CAT enzyme activity as described. Numbers represent percentage conversion of chloramphenicol to acetylated forms in one hour using equivalent amounts of protein lysate in a typical experiment. No effect on CAT activity directed by the pSV$_2$CAT plasmid, containing the SV40 early region promoter 5' to the CAT gene, was observed with any of the mutant proviruses tested.

EXAMPLE 4

RNA and protein production following transfection

Figures 5A, 5B, 5C:
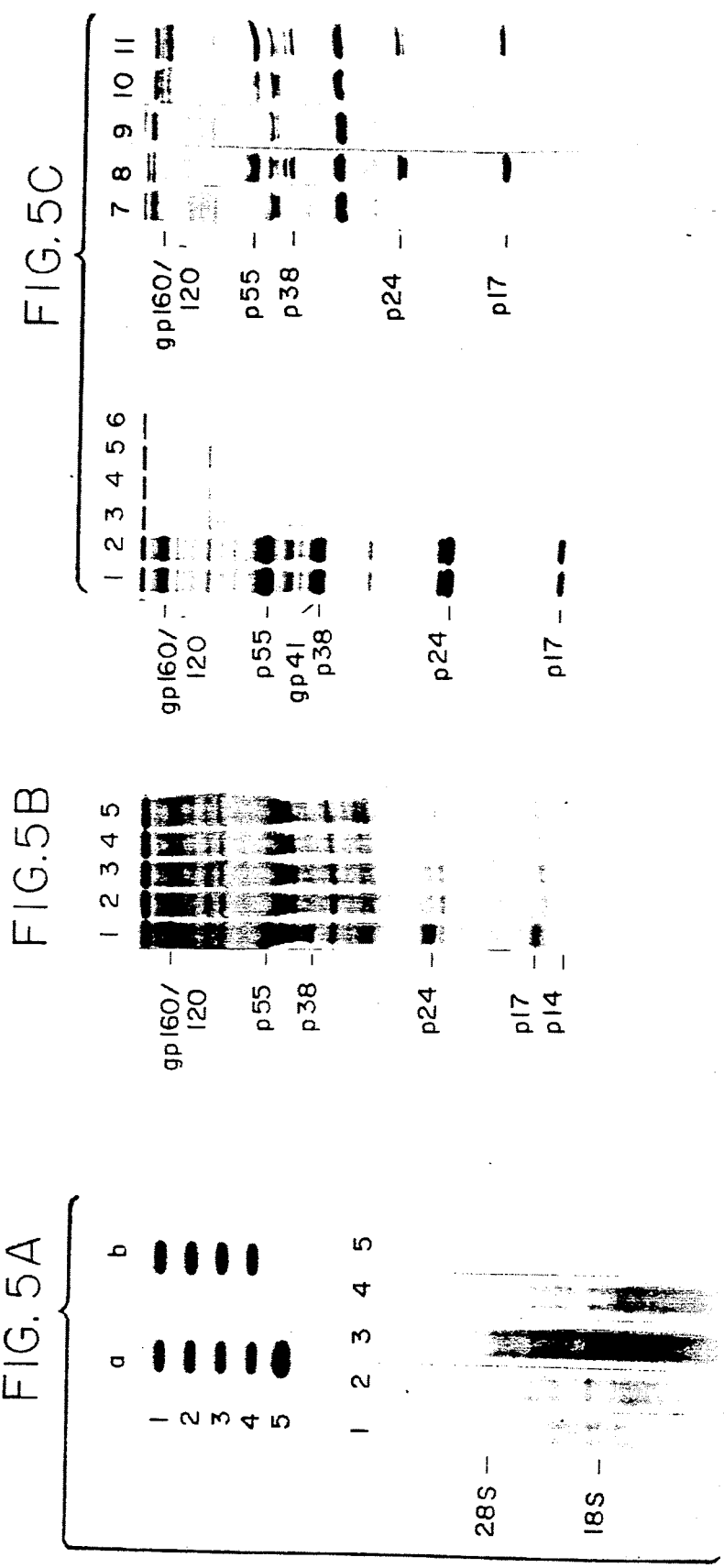
FIG. 5A illustrates RNA slot-blots from transfected cells.
FIG. 5B shows proteins immunoprecipitated from the transfected cells.
FIG. 5C shows immunoprecipitates of cells transfected with proviral plasmids using patient antiserum.

Approximately $5 \times 10^7$ Raji cells were transfected with 10 micrograms test plasmid DNA and 10 micrograms pSV$_2\beta$-globin DNA using the DEAE-dextran technique [Queen et al, *Cell* 33:741-748 (1983). Forty-eight hours post-transfection half of the cells were labelled with $^{35}$S-cysteine and immunoprecipitated with 38-1 patient antiserum as described [Lee, T. J. et al, *P.N.A.S.* (1986) supra]. The other half of the cells was used for total RNA isolation using the guanidine thiocyanate-CsCl method [Chirgwin, J. M. et al, *Biochemistry* 18:5294-5299 (1979)]. Five micrograms of RNA was slot-bloated onto duplicate nitrocellulose filters and ten micrograms were size-separated on formaldehyde gels and transferred to nitrocellulose [Thomas, P., *P.N.A.S.* 77:5201–5202 (1980)] (See FIG. 5A). One slot-blot was hybridized to a probe derived from the complete $\beta$-globin cDNA sequence (column a). The other slot-blot (column b) and the Northern blot (lower figure) was hybridized to a probe made from a pooled collection of Bgl II internal proviral fragments derived from the pHXBc2 plasmid. filters were washed as described by Thomas, P.N.A.S., supra, prior to autoradiography. Proteins immunoprectpitated from the Raji transfectants are shown in FIG. 5B. Transfected test plasmids for the Northern blot, slot blots, and protein gel are: 1) pHXBc2, 2) pΔ(8053-8474), 3) pFS8053, 4) pΔ(5365-5496) and 5) a plasmid, pCR1, containing an incomplete HTLV-I provirus. The control lanes in this figure (lanes 1 and 4) were previously published [Rosen, C. A., et al, *Nature* (1986) supra]. FIG. 5C shows immunoprecipitates of Jurkat-tat$_{III}$ cells transfected with proviral plasmids using patient antiserum RV119, as previously described. Transfected plasmids were: pHXBc2 (lanes 1 and 11), pΔ(5365–5496) (lane 2), pΔ(5365–5702) (lane 3), pΔ(8053–8474) (lane 4), pFS8053 (lane 5), pIII$\beta$-globin, containing a HTLV-III LTR 5' to rabbit $\beta$-globin cDNA sequences (lanes 6 and 7), pΔ(6617–7198) (lane 8), pΔ(5365–5551) (lane 9), and pa(5365-5439) (lane 10).

EXAMPLE 5

Expression of The Art Gene Product

Figure 6:
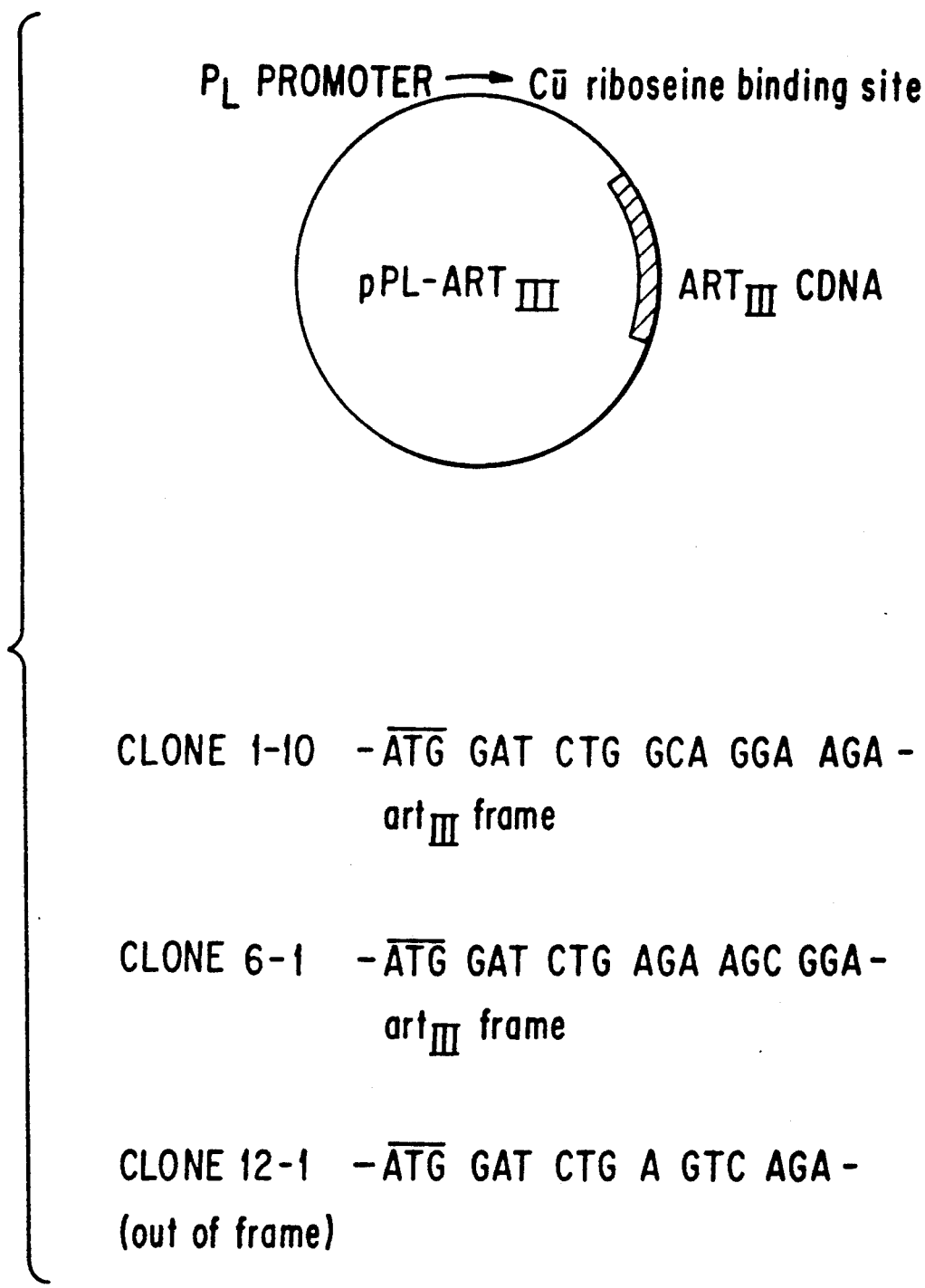
FIG. 6 shows a plasmid that is capable of producing the art protein in bacteria.

The coding region of art from an HTLV-III cDNA clone (derived from pCV4.3 HTLV-III cDNA clone [Arya et al, *Science*, supra]), as described above, was inserted into the BamHI site of an overexpression vector. Such vectors are readily available to a person of ordinary skill in the art. Indicated in FIG. 6 are the frames of two plasmids (clones 1.10 and 6.1) constructed to express the art$_{III}$ coding region. Expression is promoted from the bacteriophage lambda P$_L$ promoter. The P$_L$ promoter is normally repressed by the lambda cI repressor gene to avoid any problems of lethality due to over expression of any protein during cloning. To monitor expression orf the P$_L$ promoter, the P$_L$-art$_{III}$ plasmid is re-introduced into bacterial strains (N99cI$^{ts857}$) that carry a prophage carrying a temperature sensitive mutation in its lambda cI gene. The temperature sensitive strains are then induced at 42° C. to overexpress the art protein.

Figure 7A:
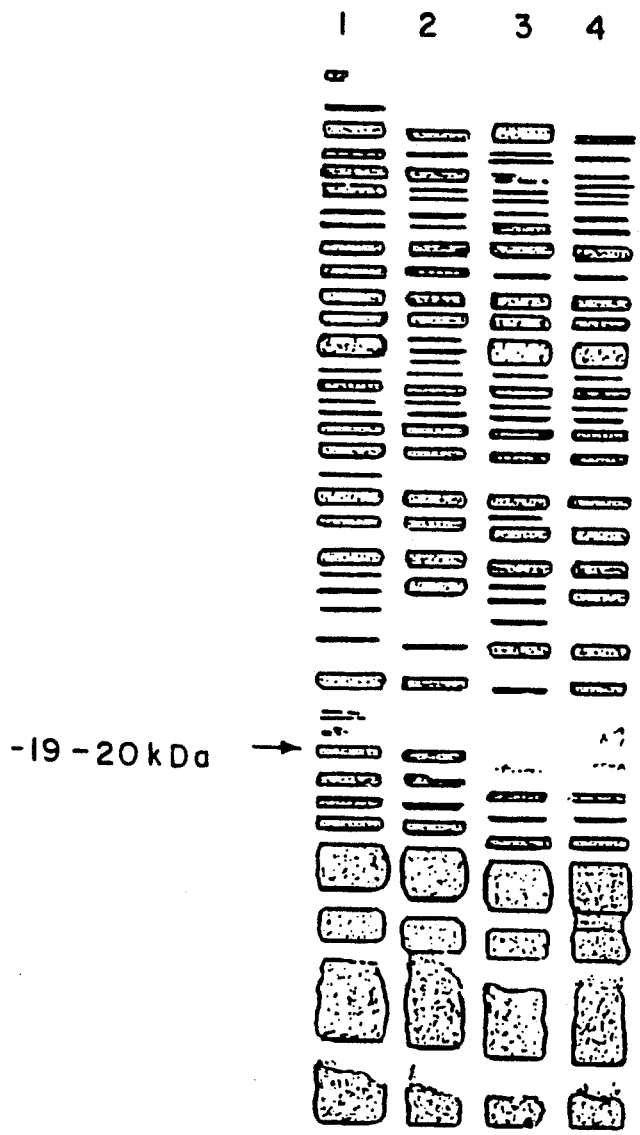

FIG. 7A shows that a protein, approximately 19 to 20 kilodaltons is induced in strains by P$_L$-art$_{III}$ at 42° C. Confirmation that this is the art product is shown by use of strains containing a plasmid with an out-of-frame art sequence (Clone 12.1). Lanes 3 and 4 of FIG. 7A indicate that this clone does not induce any protein of the same molecular weight proving that the induced protein is expressed from the P$_L$-art$_{III}$ plasmid.

FIG. 7B shows that the bacterially produced art product is recognized by AIDS patient sera. This demonstrates that the protein is made in infected patients, and is immunogenic.

EXAMPLE 6

Preparation of Multi-tiered Expression System

An expression vector was prepared using standard techniques (See, e.g., Mantarts, T., et al, *Molecular Cloning: A Laboratory Manual*, Cold Spring Harbor Laboratory 1982). This vector contained an HTLV-III LTR and the chloramphenicol acetyl transferase (CAT) gene, downstream of the HTLV-III LTR. The CAT gene was fused to a nucleotide sequence derived from the HTLV-III genome, starting with the tat$_{III}$ gene and continuing through the viral polyadenylation sequence, with the art gene excised. This nucleotide sequence was prepared by the same procedures as described in Example 3. A Jurkat tat$_{III}$ cell was transfected by the DEAE-dextran procedure using ten micrograms of the vector. Forty-eight hours after transfection, cell lysates were prepared and tested for the presence of the CAT protein. No CAT expression was detected. Subsequently, these cells were cotransfected with ten micrograms of the LTR-CAT plasmid and ten micrograms of an art expressing plasmid as described above. Thereafter, CAT expression was detected confirming the ability of the art gene to "turn on" cellular expression of a heterologous gene under the control of a cis-acting negative sequences derived from the viral genome.

All the references discussed above are incorporated herein by reference.

It is evident that those skilled in the art, given the benefit of the foregoing disclosure, may make numerous ocher uses and modification thereof, and departures from the specific embodiments described herein, without parting from the inventive concepts, and the present invention is to be limited solely by this scope and spirit of the appended claims.

We claim:

1. A purified and isolated art (rev) protein having the amino acid sequence:

MAGRSGDSDEDLLKAVRLIKFLYQS
DPPPNPEGTRQARRNRRRRWRE
RQRQIHSISERILSTYLGRSAEPVPLQLPPLE
RLTLDCNEDCGTSGTQGVGSPQILVESPTVLESGAKE.

which regulates HIV envelope protein synthesis, or a fragment thereof which retains the function of regulating HIV envelope protein synthesis.

2. The protein of claim 1 having a molecular weight of about 19 to 20 kilodaltons.

3. The protein of claim 1 which is 116 contiguous amino acids.

4. A purified and isolated art (rev) protein or a fragment thereof encoded by two coding exons of the art gene which are an alternative reading frame of the tat gene, and wherein the art protein or the fragment thereof has trans-activating function which regulates HIV envelope protein synthesis.

* * * * *